United States Patent
Chen et al.

(10) Patent No.: US 8,445,532 B2
(45) Date of Patent: *May 21, 2013

(54) USE OF PHTHALIDE DERIVATIVES

(76) Inventors: Fei Chen, Shanghai (CN); Tao Wang, Shanghai (CN)

( * ) Notice: Subject to any disclaimer, the term of this patent is extended or adjusted under 35 U.S.C. 154(b) by 717 days.

This patent is subject to a terminal disclaimer.

(21) Appl. No.: 12/088,778

(22) PCT Filed: Sep. 30, 2005

(86) PCT No.: PCT/CN2005/001627
§ 371 (c)(1),
(2), (4) Date: Mar. 31, 2008

(87) PCT Pub. No.: WO2007/036074
PCT Pub. Date: Apr. 5, 2007

(65) Prior Publication Data
US 2008/0255061 A1  Oct. 16, 2008

(51) Int. Cl.
*A61K 31/34* (2006.01)

(52) U.S. Cl.
USPC ............ 514/470; 514/462; 514/468; 549/466

(58) Field of Classification Search
None
See application file for complete search history.

(56) References Cited

U.S. PATENT DOCUMENTS

| 2004/0092583 A1 * | 5/2004 | Shanahan-Prendergast . | 514/469 |
| 2004/0109904 A1 * | 6/2004 | Li ................................ | 424/725 |
| 2006/0068045 A1 * | 3/2006 | Yong et al. .................... | 424/773 |

FOREIGN PATENT DOCUMENTS

| CN | 1087276 | 6/1994 |
| CN | 1222356 | 7/1999 |
| CN | 1569848 | 1/2005 |
| CN | 1679544 | 10/2005 |
| EP | 1 645 280 A1 | 4/2006 |
| JP | 3-157379 A | 7/1991 |
| WO | WO 2004017983 A1 * | 3/2004 |

OTHER PUBLICATIONS

"Naming Organic Compounds: A Systematic Instruction Manual," 2nd Ed., by Godly, Ellis Horwood Ltd. (Hertfordshire, UK), p. 6 (1989).*
"Acetone extract of *Angelica sinensis* inhibits proliferation of human cancer cells via inducing cell cycle arrest and apoptosis," by Cheng et al., Life Sciences 75, 1579-94 (2004).*
"Liquid chromatographic-electrospray mass spectrometric study of the phthalides of *Angelica sinensis* and chemical changes of Z ligistulide," by Lin et al., J. Chromatogr. A, 810, 71-79 (1998).*
"Molecular targeting therapy of cancer: drug resistance, apoptosis and survival signal" by Tsuruo et al., Cancer Sci. 94, 15-21 (2003).*
Zheng at al. "Chemoprevention of Benzo[α]pyrene-Induced Forestomach Cancer in Mice by Natural Phthalides from Celery Seed Oil". Nutr-Cancer 19(1), 1993, p. 77-86.
Mullady et al. "A Phthalide with in Vitro Growth Inhibitory Activity from an *Oidiodendron* Strain". Journal of Natural Products 67(12), 2004, p. 2086-2089.
Qisheng et al. "Investigation Advance of phthalides". Journal of Jiangxi College of Traditional Chinese Medicine 8(1), 1996, p. 46-47.
International Search Report for PCT/CN2005/001627.
Zhang et al., "Characterization of phthalides in *Ligusticum chuanxiong* by liquid chromatographic-atmospheric pressure chemical ionization-mass spectrometry," Journal of Chromatographic Science, 2003, vol. 41, pp. 428-433.
Zheng et al., "Chemoprevention of benzo[a]pyrene-induced forestomach cancer in mice by natural phthalides from celery seed oil," Nutrition and Cancer, 1993, vol. 19, No. 1, pp. 77-86.
Lin et al., "Liquid chromatographic-electrospray mass spectrometric study of the phthalides of *Angelica sinensis* and chemical changes of Z-ligustilide," Journal of Chromatography A, 1998, vol. 810, pp. 71-79.
Mullady et al., "A phthalide with in vitro growth inhibitory activity from an *Oidiodendron* Strain," Journal of Natural Products, 2004, vol. 67, No. 12, pp. 2086-2089.
Li et al., "Simultaneous analysis of seventeen chemical ingredients of *Ligusticum chuanxiong* by on-line high performance liquid chromatography-diode array detector-mass spectrometry," Planta Med, 2003, vol. 69, No. 5, pp. 445-451.

* cited by examiner

*Primary Examiner* — Brandon Fetterolf
*Assistant Examiner* — Theodore R West
(74) *Attorney, Agent, or Firm* — Hamre, Schumann, Mueller & Larson, P.C.

(57) ABSTRACT

Phthalide derivatives and the use of which to manufacture the sensitizer or reverser of the antineoplastic agent are described. The phthalide derivatives can enhance the sensitivity of drug-resistance tumor cells against chemotherapy and decrease the drug-resistance of tumor cells 5-30 folder and enhance notably several chemotherapy agents-induced apoptosis of tumor cells.

5 Claims, 3 Drawing Sheets

USE OF PHTHALIDE DERIVATIVES

TECHNICAL FIELD

The present invention relates to the use of phthalide derivatives (PA). The monomers and dimers of these derivatives can enhance the sensitivity of drug-resistant tumor cells to chemotherapeutic drug.

BACKGROUND ART

Multi-drug resistance (MDR) means that the tumor cells have cross-resistance to various anti-cancer drugs with different chemical structure, function and mechanism. Clinical study shows that some solid tumors such as colonic cancer, renal cancer, hepatocarcinoma, non-small cell lung cancer, glioma, kaposis sarcoma, and prostate cancer are generally drug resistant, even probably at the time when they are just been diagnosed, thus belonging to intrinsic MDR. In these tumor cells, there are usually various resistance mechanisms concurrently provoking a broad resistance to chemotherapeutic drugs. Whilst, some tumors such as acute myeloid leukemia, acute lymphocytic leukemia, multiple myeloma, lymphoma, mammary cancer, and ovary cancer are generally sensitive to chemotherapeutic drugs at the initial treatment stage but become drug-resistant gradually during the treatment, especially during the treatment of recurrence when the drug-resistance significantly increases. This type of drug-resistance is called acquired MDR. The therapeutic effect would fall notably after the establishment of the drug-resistance. MDR results in poor therapeutic effect, bad prognosis and easy tumor recurrence and metastasis of the conventional chemotherapies. About 90% of the dead cases in tumor patients are associated with the intrinsic or acquired drug-resistance.

The mechanisms of the occurrence of MDR have been studied widely. Seen as a whole, MDR is co-regulated by multiple factors and multiple mechanisms, mainly including the efflux of chemotherapeutic drugs by ABC transfer proteins, the enhanced expression of anti-apoptosis proteins, the alteration of metabolic pathway and regulating mode, and the enhancement of detoxification system.

Therefore, a chemotherapeutic sensitizer with notable effect is urgently needed in the prior art.

CONTENTS OF THE INVENTION

The purpose of the present invention is to provide chemotherapeutic sensitizers with notable effect, and use of the same in the manufacture of sensitizers or reversers for anti-tumor chemotherapy. Said sensitizers are the phthalide or derivatives thereof of formula (I) (including monomers and dimers).

In the first aspect, the present invention provides use of the phthalide or derivative thereof of formula (I) in the manufacture of a sensitizer or reverser of anti-tumor drugs.

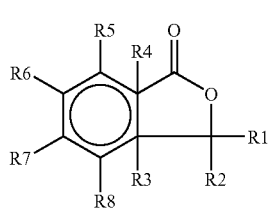

(I)

wherein,

R1 is hydrogen, hydroxyl, C1-C8 alkyl, C2-C8 alkenyl, C2-C8 alkynyl, C3-C8 cycloalkyl, C1-C8 alkoxyl, C1-C4 carboxyl, or halogen;

R2 is hydrogen, hydroxyl, C1-C8 alkyl, C2-C8 alkenyl, C2-C8 alkynyl, C3-C8 cycloalkyl, C1-C8 alkoxyl, C1-C4 carboxyl, or halogen, or R2 is absent;

R3 and R4 are independently hydrogen, hydroxyl, C1-C8 alkyl, C2-C8 alkenyl, C2-C8 alkynyl, C3-C8 cycloalkyl, C1-C8 alkoxyl, or halogen;

R5 and R8 are hydrogen, hydroxyl, C1-C8 alkyl, C2-C8 alkenyl, C2-C8 alkynyl, C3-C8 cycloalkyl, C1-C8 alkoxyl, C1-C4 carboxyl, phenyl, aryl, aralkyl, 5-6-membered heterocyclic ring which contains 1-2 nitrogen atoms, or halogen;

R6 and R7 are independently hydrogen, hydroxyl, C1-C8 alkyl, C2-C8 alkenyl, C2-C8 alkynyl, C1-C4 carboxyl, or halogen; or R6 and R7 are linked together to form a 5-7-membered ring;

wherein, the alkyl, alkenyl, alkynyl, cycloalkyl, alkoxyl, phenyl, aryl, aralkyl and heterocyclic ring are substituted by 0-3 substituents selected from the group consisting of C1-C3 alkyl, hydroxyl, and halogen.

In another preferable embodiment, said derivative is the two-hydrogen derivative or four-hydrogen derivative of the phthalide of formula (I), or the dimer of the phthalide of formula (I), the two-hydrogen derivative or four-hydrogen derivative.

More preferably, the structure of said phthalide or derivative thereof is selected from:

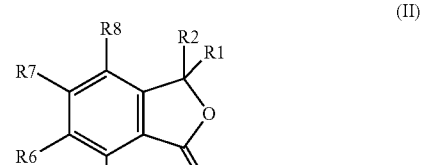

(II)

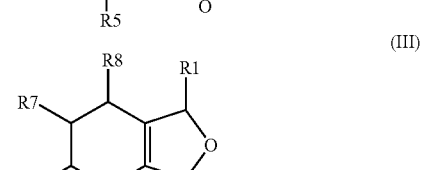

(III)

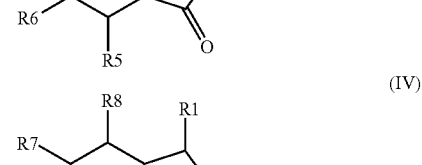

(IV)

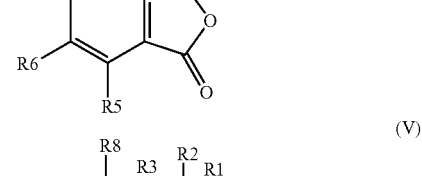

(V)

wherein, R1~R8 are defined as above.

In another preferable embodiment, the structure of said phthalide or derivative thereof is selected from:
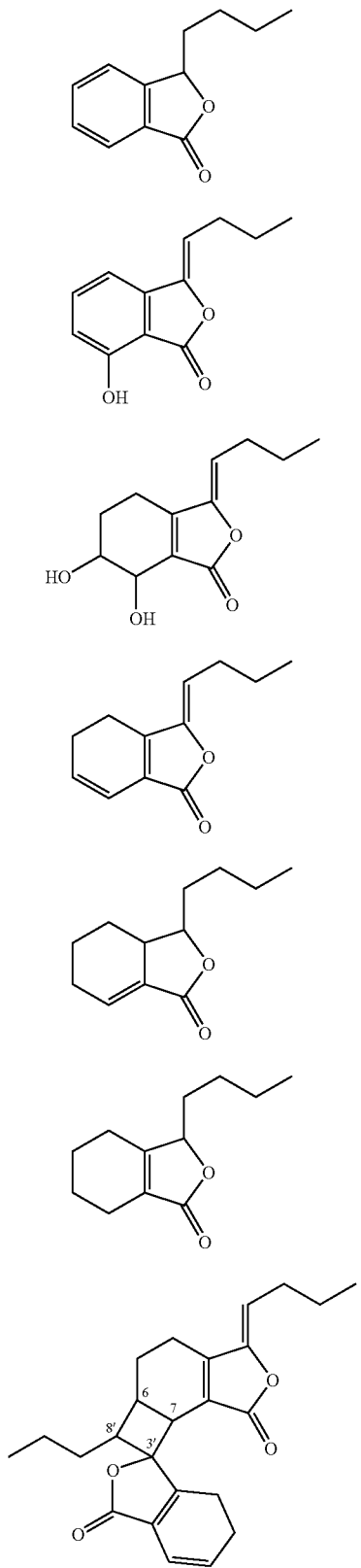
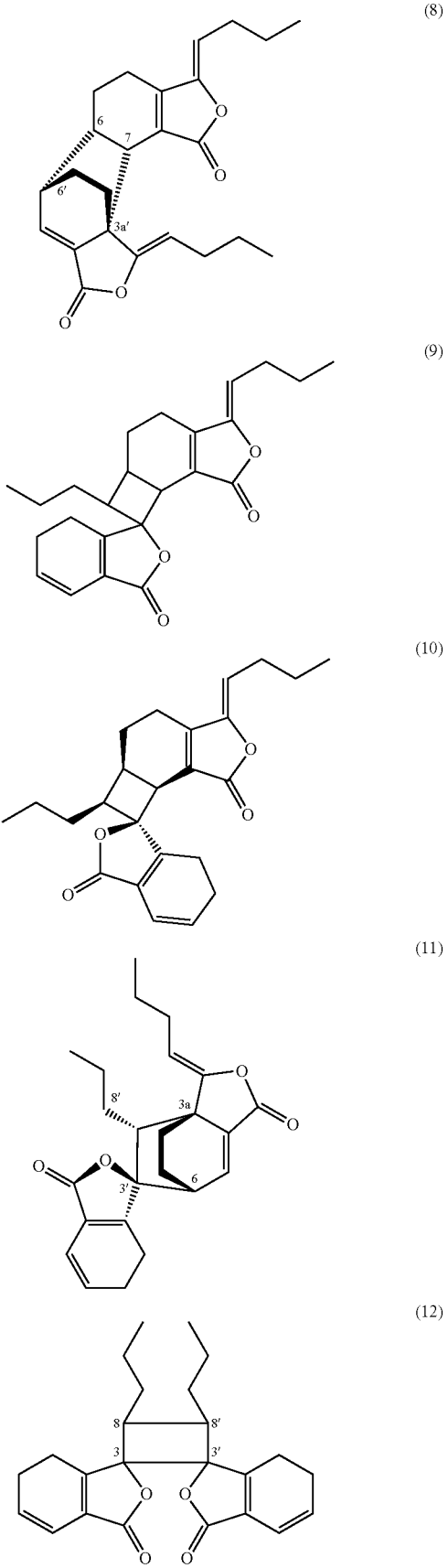

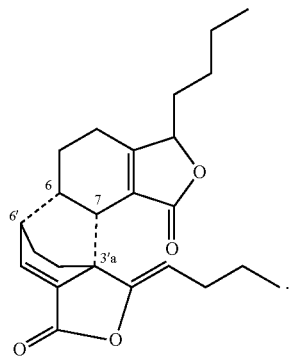
(13)

Preferably, said anti-tumor drugs are selected from: ADRIAMYCIN® (doxorubicin); Vincristine; TAXOL® (paclitaxel); Cisplatin; Actinomycin; Bleomycin; Busulfan; Capecitabine; Carboplatin; Carmustine; Chlorambucil; Cyclophosphamide; Cytarabine; Daunorubicin; Epirubicin; Etop1; Vepeside; Etoposide; Fludarabine; Fluorouracil; Gemcitabine; Trastuzumab; Hydroxycarbamide; Idarubicin; Ifosfamide; Irinotecan; Lomustine; Melphalan; Mercaptopurine; Methotrexate; Mitomycin; Mitoxantrone; Dihydroxyanthraquinone1; Oxaliplatin; Procarbazine; Methylhydrazine; MabThera® (rituximab); Steroid; Streptozocin; Streptozocin; Docetaxel; Thioguanine; Thiotepa; Ledertepa; Tespamin; Raltitrexed; Topotecan; Treosulfan; Uracil; Vinblastine; Vinca alkaloid; Vindesine; Vinorelbine; Glivec; Hydroxycamptothecin; and derivatives or mixtures thereof.

In another preferable embodiment, said anti-tumor drugs are used to treat tumors selected from the group consisting of: non-small cell lung cancer, prostate cancer, intestinal cancer, hepatocarcinoma, leukaemia, myeloma, lymphoma, mammary cancer, ovary cancer, gastric cancer, esophagus cancer, colonic cancer, or sarcoma.

In the second aspect, the present invention provides a pharmaceutical composition, which comprises (a) an effective amount of the phthalide or derivative thereof of formula (I), (b) a safe and effective amount of anti-tumor drug, and (c) a pharmaceutically acceptable vehicle.

Preferably, said anti-tumor drug is selected from the group consisting of: ADRIAMYCIN® (doxorubicin); Vincristine; TAXOL® (paclitaxel); Cisplatin; Actinomycin; Bleomycin; Busulfan; Capecitabine; Carboplatin; Carmustine; Chlorambucil; Cyclophosphamide; Cytarabine; Daunorubicin; Epirubicin; Etop1; Vepeside; Etoposide; Fludarabine; Fluorouracil; Gemcitabine; Trastuzumab; Hydroxycarbamide; Idarubicin; Ifosfamide; Irinotecan; Lomustine; Melphalan; Mercaptopurine; Methotrexate; Mitomycin; Mitoxantrone; Dihydroxyanthraquinone1; Oxaliplatin; Procarbazine; Methylhydrazine; MabThera® (rituximab); Steroid; Streptozocin; Streptozocin; Docetaxel; Thioguanine; Thiotepa; Ledertepa; Tespamin; Raltitrexed; Topotecan; Treosulfan; Uracil; Vinblastine; Vinca alkaloid; Vindesine; Vinorelbine; Glivec; Hydroxycamptothecin; and derivatives or mixture thereof.

In the third aspect, the present invention provides use of the phthalide or derivative thereof of formula (I) in the manufacture of a composition that overcome P-gp or Bcl-2 overexpression, or glyoxylase I over-activity.

In the fourth aspect, the present invention provides a method of treating tumor comprising administering to a mammalian in need of such treatment a safe and effective amount of the phthalide or derivative thereof of formula (I).

Preferably, said method further comprises administering at least one anti-tumor drug described above.

MODE OF CARRYING OUT THE INVENTION

Figure 1:
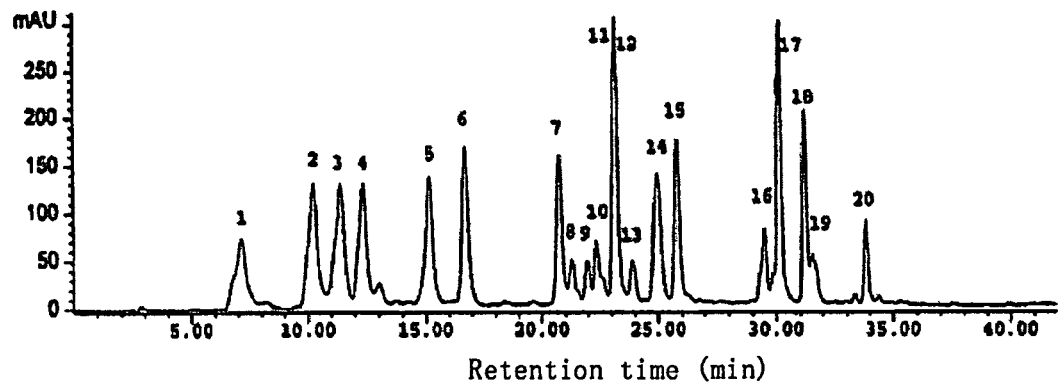
FIG. 1 shows the chromatogram of phthalide derivatives.

Inventors of the present invention, through an extensive and intensive investigation, have found that the phthalide and derivatives thereof of formula (I) thereof are effective sensitizers of anti-tumor chemotherapeutics. Based on the sensitizing action, phthalide and derivatives thereof can effectively reverse the multi-drug resistance of tumor to anti-tumor drugs. This constitutes the basis of the present invention.

As used herein, the term "alkyl" refers to a straight or branched, saturated aliphatic hydrocarbon group containing 1-8 (preferably 1-6) carbon atoms. Said alkyl may be branched, for example, methyl, ethyl, n-propyl, iso-propyl, n-butyl, iso-butyl, tert-butyl, n-pentyl, iso-pentyl, tert-pentyl, hexyl etc. The term "alkenyl" refers to an straight or branched hydrocarbon group containing at least one C—C double bond and 2-8 (preferably 2-6) carbon atoms. The term "alkynyl" refers to a straight or branched hydrocarbon group containing at least one C—C triple bond and 2-8 (preferably 2-6) carbon atoms.

As used herein, the term "aryl" refers to an aromatic system, which may be a monocyclic ring or a multi-cyclic aryl ring that formerly fused or linked together so that at least part of the fused or linked ring would form conjugated aromatic system. The aryl group includes (but not limited to): phenyl, naphthyl, and tetralyl.

As used herein, the term "cycloalkyl" refers to a cycloalkyl group with 3-8 carbon atoms, such as cyclopropyl, cyclopentyl, cyclohexyl and cycloheptyl, etc.

The term "alkoxyl" refers to an alkoxyl with 1-8 carbon atoms, such as methoxyl, ethoxyl, propoxyl, butoxyl, amoxyl, hexoxyl, etc.

The term "heterocyclic ring" refers to a stable 4-7 (preferably 5-6)-membered monocyclic ring or a stable multi-cyclic heterocyclic ring. Said heterocyclic ring may be saturated, partly unsaturated or unsaturated and consists of carbon atoms and 1-4 hetero-atoms selected from: N, O and S. The N and S atoms may be oxidized. The heterocyclic ring may further include any multiple-ring, and anyone of the heterocyclic ring mentioned above may fuse to an aryl ring.

"Substituted aryl" or "substituted heterocyclic ring" refers to an aryl group or heterocyclic ring that is substituted by a substituent selected from the group consisting of: halogen, CN, OH, $NO_2$, amino, alkyl, cycloalkyl group, alkenyl, alkynyl, alkoxyl, aryloxy, substituted alkoxyl, alkylcarbonyl, alkylcarboxyl, alkylamino or arylsulfonyl. Preferably, the substituent is halogen, C1-C4 alkyl, alkyl, or hydroxyl.

As used herein, the term "halogen" refers to a halogen family element, which is F, Cl, Br or I.

Active Ingredients

The active ingredients of the present invention are the phthalide derivatives of formula (I).

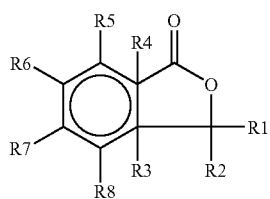

(I)

As used herein, the term "phthalide derivative" refers to the phthalide of formula (I), wherein the phthalide derivative monomer may have hydrogen attached on phenyl. This term also includes the dimers or polymers (preferably, dimmers) of the phthalide of formula (I) or the hydrogenated products thereof.

As used herein, the term "two hydrogen derivative" means that two hydrogen atoms are added on the adjacent carbon atoms corresponding to the double bond in the phenyl ring of the phthalide. The term "four hydrogen derivative" means that four hydrogen atoms are added on the adjacent carbon atoms corresponding to the double bonds in the phenyl ring of the phthalide. For example, the compound of formula (k)' is a two hydrogen derivative of the compound of formula (k); the compound of formula (k)" is a four hydrogen derivative of the compound of formula (k).

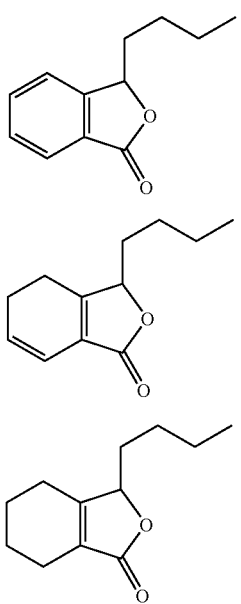

(k)

(k)'

(k)"

The phthalide derivatives of the present invention can be artificially synthesized or isolated from the nature. For example, the monomer and/or dimer of phthalide of formula (I) can be isolated by extracting from the angelica or ligusticus wallichii franchet of umbelliferous plants.

Pharmaceutical Composition

The present invention further includes a pharmaceutical composition, which comprises the phthalide derivative of formula (I) (monomer or dimer) as an active ingredient and one or more pharmaceutically acceptable vehicle or excipient (such as solvent, diluent). The pharmaceutically acceptable vehicle that can be used in the present invention includes various conventional solid vehicle and liquid vehicle, as long as they suit the characteristics of the active ingredient and the desired specific administration mode. For example, the solid vehicle includes: starch, lactose, $CaHPO_4$, microcrystalline cellulose, etc. and the liquid vehicle includes: sterile water, polyethylene glycol, etc.

The pharmaceutical composition of the present invention may be prepared into various conventional forms, such as tablet, capsule, dispersible powder, granule, suspension, syrup (comprising, for example, about 10-50% sugar), and elixir (comprising about 20-50% ethanol). The form of the pharmaceutical composition may also be sterile injectable solution or suspension (about 0.05-5% suspending agent in isotonic medium) for parenteral administration. For example, the pharmaceutical formulation may comprise 0.01-99.9 wt %, preferably 2.5-90 wt %, more preferably 5-60 wt % of the active ingredient admixed with a vehicle.

In another preferable embodiment, the pharmaceutical composition further comprises an anti-tumor drug. For example, the pharmaceutical composition comprises (a) 0.01-99 wt % (preferably 0.1-90 wt %) of the monomer or dimer of the phthalide derivative; (b) 0.01-99 wt % (preferably 0.1-90 wt %) of an anti-tumor drug; (c) a pharmaceutically acceptable vehicle. Generally, the weight proportion of component (a) and component (b) is 1:100~100:1, preferably 10:1~1:10.

The pharmaceutical composition may further comprise other additives, such as pigment, preservative and antioxidant, etc.

The effective dosage of the active component may change depending upon the administration scheme and the severity of the disease to be treated. However, the effect will be satisfying when the monomer or dimer of the phthalide derivative is administered in the dosage of about 0.05-500 mg/kg body weight (preferably 0.1-100 mg/kg body weight) per day. Preferably, 2-4 separate doses may be administered daily, or administered in a slow-released form.

Treatment Method

The present invention further provides a treatment method comprising the step of administering a safe and effective amount of the monomer or dimer of the phthalide derivative to a mammalian in need of such treatment. Preferably, said method further comprises the step of: concurrently administering other anti-tumor drugs (such as an anti-tumor drug as the substrate for P-gp) or other therapeutic means (such as chemotherapy).

Various tumors can be treated by administration of the monomer or dimer of the phthalide derivative alone or in combining with other agents. The representative examples include (but not limited to) non-small cell lung cancer, prostate cancer, intestinal cancer, hepatocarcinoma, leukaemia, myeloma, lymphoma, mammary cancer, ovary cancer, gastric cancer, esophagus cancer, colonic cancer, sarcoma, etc.

There is not any special limitation in the administration mode of the monomer or dimer of the phthalide derivative. They may be administered orally, intravenously, intramuscularly, topically, intratumorally or subcutaneously, etc. Preferably they are administered orally, intravenously or intratumorally.

The main advantage of the present invention is:

All the monomers or dimers of the phthalide derivatives according to the present invention can widely enhance the sensitivity of tumor cells to anti-tumor drugs and reverse the multi-drug resistance (MDR), thereby effectively improving the ability of the anti-tumor drugs to kill tumor cells. The experiments have proved that they have better reverse effect than Verapamil (VER, a P-gp inhibitor) when combined with anti-tumor drugs such as Adriamycin (Adr) for killing drug-resistant tumor cells. When they are administered with Vincristine (VCR), Taxol or Cisplatin (DDP), the reverse effect is over 2-5 folds better than that of Verapamil. Such derivatives can decrease the drug resistance of tumor cells by 5-30 folds, and dramatically increase tumor cell apoptosis induced by numerous chemotherapeutic drugs.

The present invention will be further illustrated by the following examples. It would be appreciated that, these examples are only intended to illustrate the invention, but not to limit the scope of the invention. For the experimental methods in the following examples, they are performed under routine conditions or as instructed by the manufacturers, unless otherwise specified.

EXAMPLE 1

Extraction of Phthalide Derivatives from Ligusticus Wallichii Franchet and Angelica 3 kg medicinal materials (ligusticus wallichii franchet or angelica) were dried and crushed, and filtrated with 20-mesh sieve. The resulting powder was extracted for 3 times by a double volume (v/w) of chloroform. The chloroform was removed from the extracting solution and the remaining solution was condensed into extractum. The extractum was then extracted by n-hexane and methanol. The methanol phase was flowed through G254 silica gel chromatographic column repeatedly, n-hexane and acetonitrile (in the volume proportion of 9:1 to 5:5) as eluent, to give the compounds S1-S5, which correspond to the peak of 8, 12, 7, 14, 3 in FIG. 1, respectively. The n-hexane phase was flowed through G254 silica gel chromatographic column repeatedly, ligroin and acetic ester (in the proportion of 9:1 to solely acetic ester) as eluent, to give the compounds S6-S8 that correspond to the peak of 16, 18, 17 in FIG. 1, respectively. Each of these monomers was dissolved in a suitable polar liquid and recrystallized by over-saturation at room temperature for 2-3 times. The resultant crystal was identified by NMR.

The compounds of S1-S5 are monomers of PA derivatives, and the compounds of S6-S8 are dimers of PA derivatives.

S1:

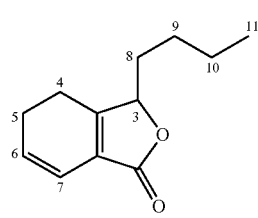

$^1$H-NMR (CDCl$^3$) δ 4.96 (1H, dd, J=6.5, 4.0, H-3) 2.45 (4H, m, H-4, H-5) 5.88 (1H, dt, J=10.0, 3.5, H-6) 6.16 (1H, dt, J=10.0, 1.0, H-7) 1.51 (1H, m, H-8a), 1.85 (1H, m, H-8b) 1.36 (4H, m, H-9H-10) 0.87 (3H, t, J=7.5, H-11)

S2:

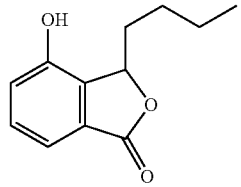

$^1$H-NMR (CDCl$^3$) δ 5.52 (1H, dd, J=8.0, 3.2, H-3), 7.33 (1H, dd, J=7.5, 1.4, H-5), 7.31 (1H, t, J=7.5, H-6), 7.10 (1H, dd, J=7.5, 1.4, H-7), 2.31 1.73 (each 1H, m, H-8), 1.37 (4H, m, H-9, H-10), 0.89 (3H, t, J=7.1, H-11), 9.59 (1H, s, 4-OH)
$^{13}$C-NMR (CDCl$_3$) δ 171.2 (s, C-1) 80.9 (d, C-3) 136.1 (s, C-3a) 152.4 (s, C-4) 120.2 (d, C-5) 130.3 (d, C-6) 115.9 (d, C-7) 127.8 (s, C-7a) 32.3 (t, C-8) 26.9 (t, C-9) 22.4 (t, C-10) 13.9 (q, C-11)

S3:

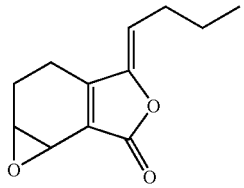

$^1$H-NMR δ 2.59 (2H, m, H-4) 2.06, 2.14 (each 1H, m, H-5) 4.33 (1H, ddd, J=5.5, 3.5, 2.5, H-6) 4.61 (1H, brd, J=2.5, H-7) 5.36 (1H, t, J=8.0, H-8) 2.38 (2H, m, J=8.0, 7.5, H-9) 1.58 (2H, m, J=7.5, 7.5, H-10) 0.96 (3H, t, J=7.5, H-11)

S4:

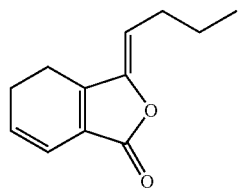

$^1$H-NMR (CDCl$^3$) δ 2.47 (2H, m, H-4) 2.57 (2H, t, J=13.5, H-5) 5.96 (1H, dt, J=9.5 4.0, H-6) 6.24 (1H, dt, J=9.5, 1.5, H-7) 5.19 (1H, t, J=8.0, H-8) 2.33 (2H, q, J=7.5H-9) 1.47 (2H, m, H-10) 0.92 (3H, t, J=7.5, H-11)

S5:

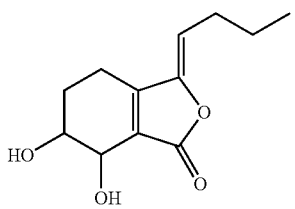

$^1$H-NMR (CDCl$^3$) δ 2.01, 1.91 (2H, m, H-4); 1.92, 1.67 (2H, m, H-5); 3.46 (1H, q, H-5); 3.77 (1H, d, H-7); 5.13 (1H, t, H-8); 1.96 (2H, m, H-9); 1.37 (2H, m, H-10); 0.96 (3H, t, H-11); 2.0 (1H, m, 6-OH, 7-OH)

S6:

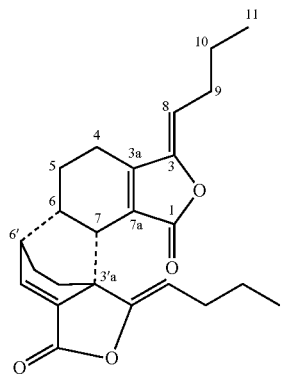

¹H-NMR (CDCl³) δ 2.02, 2.08 (each 1H, m, H-4) 1.54, 1.91 (each 1H, m, H-5) 2.55 (1H, t, J=7.8, H-6) 3.25 (1H, d, J=8.9, H-7) 5.7 (1H, t, J=7.8, H-8) 2.29 (2H, q, J=7.3, H-9) 1.46 (2H, m, H-10) 0.93 (3H, t, J=7.3, H-11) 1.4, 2.03 (1H, m, H-4') 1.30, 1.88 (1H, m, H-5') 2.99 (2H, m, H-6') 7.36 (1H, d, J=6.6, H-7') 5.0 (1H, t, J=7.6, H-8') 2.18 (2H, m, H-9') 1.45 (2H, m, H-9') 0.92 (3H, t, J=7.3)

¹³C-NMR (CDCl³) δ 168.4 (C-1), 148.1 (C-3), 155.0 (C-3a), 19.8 (C-4), 29.0 (C-5), 38.4 (C-6), 41.6 (a, C-7), 126.6 (C-7a), 112.1 (C-8), 28.0 (C-9), 22.3 (C-10), 13.9 (b, C-1'), 164.9 (C-1'), 150.5 (C-3'), 47.6 (C-3'a), 31.1 (C-4'), 25.8 (C-5'), 41.5 (a, C-6'), 142.0 (C-7'), 134.3 (C-7'a), 108.8 (C-8'), 27.5 (C-9'), 22.3 (C-10'), 13.8 (b, C-11')

S7:

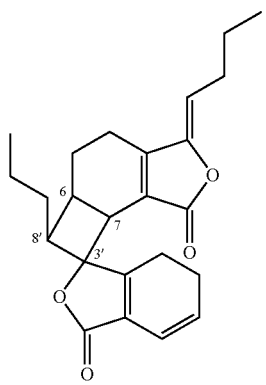

¹H-NMR (CDCl³) δ 2.02, 2.57 (each 1H, m, H-4) 2.02, 2.17 (each 1H, m, H-5) 2.55 (1H, m, H-6) 3.47 (1H, d, J=7.3, H-7) 5.21 (1H, t, J=7.8, H-8) 2.33 (2H, m, H-9) 1.50 (2H, m, H-10) 0.95 (3H, t, J=7.6, H-11) 2.58, 2.74 (each 1H, m, H-4') 2.47, 2.75 (each 1H, m, H-5') 5.93 (1H, dt, J=9.6, 4.1, H-6') 6.17 (1H, dt, J=9.6, 1.8, H-7') 2.94 (1H, q, J=7.8, H-8') 1.45 (2H, m, H-9') 1.14 (2H, m, H-10') 0.87 (3H, t, J=7.6, H-11')

¹³C-NMR (CDCl³) δ 168.5 (C-1), 149.2 (C-3), 154.6 (C-3a), 19.6 (C-4), 26.2 (C-5), 35.0 (c, C-6), 44.0 (C-7), 122.3 (c, C-7a), 112.2 (C-8), 28.0 (C-9), 22.4 (C-10), 13.9 (C-11), 170.3 (C-1'), 92.0 (C-3'), 160.1 (C-3'a), 21.0 (c, C-4'), 20.7 (c, C-5'), 138.7 (C-6'), 117.0 (C-7'), 122.5 (d, C-7'a), 32.3 (c, C-8'), 20.0 (c, C-9'), 22.6 (C-10'), 14.1 (C-11')

S8:

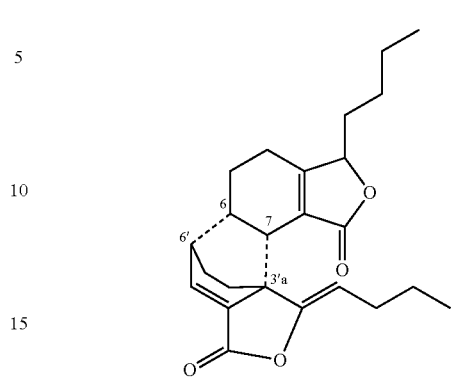

¹H-NMR (CDCl³) 54.56 (1H, m, H-3) 1.98, 2.08 (each 1H, m, H-4) 1.53, 1.90 (each 1H, m, H-5) 2.54 (1H, m, H-6) 3.18 (1H, d, J=8.9, H-7) 1.38, 1.70 (each 1H, m, H-8) 1.26 (2H, m, H-9) 1.45 (2H, m, H-10) 0.93 (3H, t, J=7.34, H-11) 1.40, 2.03 (each 1H, m, H-4') 2.30, 1.87 (each 1H, m, H-5') 2.97 (1H, m, H-6') 7.33 (1H, d, J=6.6, H-7') 4.98 (1H, t, J=7.3) 2.18 (2H, q, J=7.8, H-9') 1.44 (2H, m, H-10') 0.93 (3H, t, J=7.3, H-11')

¹³C-NMR (CDCl³) δ 165.0 (C-1), 82.4 (C-3), 47.3 (C-3a), 30.9 (C-4), 25.7 (C-5), 41.6 (C-6), 141.9 (C-7), 134.5 (C-7a), 32.2 (C-8), 26.5 (C-9), 22.3 (C-10), 13.7 (C-11), 171.9 (C-1'), 150.5 (C-2'), 168.1 (C-3a), 22.4 (C4'), 28.8 (C-5'), 38.3 (C-6'), 41.7 (C-7'), 127.1 (C-7'a), 108.6 (C-8'), 27.4 (C-9'), 22.2 (C-10'), 13.9 (C-11')

The monomers or dimers of PA derivatives of S1-S8 obtained as described above were used in the following examples. The compounds of S1-S5 are monomers of PA derivatives, and the compounds of S6-S8 are dimers of PA derivatives.

EXAMPLE 2

Drug-Resistance Determination of the Cell Lines

The following cell lines were used: K562 (human chronic myeloid leukemia cell line) and K562/Adr (a cell line with drug-resistance to chemotherapeutic drugs such as Adriamycin induced by a long-term exposure to a low dosage of Adriamycin); KB (human oral epithelia cell line) and KBv200 (a cell line with drug-resistance to chemotherapeutic drugs such as Vincristine induced by a long-term exposure to a low dosage of Vincristine); MCF-7 (human mammary cancer cell line) and MCF-7/Adr (a cell line with drug-resistance to chemotherapeutic drugs such as Adriamycin induced by a long-term exposure to a low dosage of Adriamycin). All the cell lines mentioned above were purchased from Institute of Hematology, Chinese Academy of Medical Sciences.

The multi-drug resistant cell line of K562/Adr is mainly characterized by the concurrency of multiple resistant mechanisms including the increased expression of P-gp and Bcl-2 family proteins, and the enhanced activity of glyoxalase I, etc. K562/Adr is resistant to Adriamycin 20 folds more than K562, and cross-resistant to Vincristine, Daunomycin, Mitoxantrone, Taxol, etc.

The multi-drug resistant cell line, of KBv200 is also mainly characterized by the concurrency of multiple resistant mechanisms including the increased expression of P-gp and Bcl-2 family proteins, and the enhanced activity of glyoxalase I, etc. KBv200 is resistant to Vincristine more than 100 folds in comparison with KB, and cross-resistant to Vincristine, Daunomycin, Mitoxantrone, Taxol, etc.

Similarly, the multi-drug resistant cell line of MCF-7/Adr is also mainly characterized by the concurrency of multiple resistant mechanisms including the increased expression of P-gp and Bcl-2 family proteins, and the enhanced activity of glyoxalase I, etc.

Half-inhibitory concentration ($IC_{50}$) was calculated by the GraphPad Prism software (San Diego, Calif.). Drug reaction was analyzed by Sigmoldal non-linear regression model.

The reagents and instruments used were as follows:

Solution of monomer and dimer of PA: the compound was dissolved in DMSO to prepare a working solution of 5 mg/mL, and then RPMI 1640 medium was used to prepare working solution. Adriamycin (Adr), Vincristine (VIN), Taxol, cisplatin (DDP), RPMI 1640, MTT, fetal bovine serum, culture plate, Carbon dioxide Culture Box, Enzyme Labeling Instrument, High Performance Liquid Chromatograph (HPLC), Fluorescence Activated Cell Sorter (FACS), P-gp fluorescence antibody kit UIU2 (purchased from Immunotech A Coulter Company, France).

1. Expression of P-gp Determined by FACS

The cells at logarithmic phase were collected and washed by PBS for two times. The expression of P-gp was determined by FACS according to the instructions in the P-gp fluorescence antibody kit (UIU2). 10,000 cells were counted per sample.

Results:

K562: the positive rate of P-gp expression was 0.22%; K562/Adr: the positive rate of P-gp expression was 83.6%.

KB: the positive rate of P-gp expression was 0.37%; KBv200: the positive rate of P-gp expression was 76.3%.

MCF-7: the positive rate of P-gp expression was 0.36%; MCF-7/Adr: the positive rate of P-gp expression was 83.4%.

These results demonstrate that the main drug-resistant mechanism of all the cell lines tested may be associated to the high expression of P-gp.

3. Determination of the Bcl-2 Expression

The cells were lysed in the NP-40 cell lysis solution and quantitatively analyzed by BCA. The proteins were separated on 1.2% SDS-PAGE gel and transferred to a cellulose nitrate membranes when the gel was half-dry. A primary antibody (Sigma Inc.) against Bcl-2 was added to the membrane and visualized.

Figure 2:
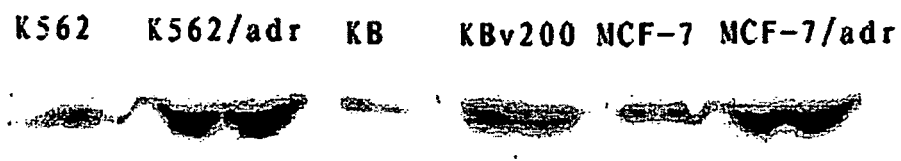
FIG. 2 shows the results of Western blot assay for Bcl-2 expression.

The results are shown in FIG. 2. The results indicate that one of the drug-resistant mechanisms of the cell lines tested is related to the high expression of Bcl-2.

2. Drug Resistance Determination of the Drug-Resistant Cell Lines to Conventional Chemotherapeutic Drugs The cells at logarithmic phase were collected and added into RPMI 1640 medium (containing 10% fetal bovine serum) to prepare a cell suspension. Then the cell suspension was plated onto a 96-well plate at 100 μl per well ($1 \times 10^4$ cell/well). Adriamycin, Vincristine, Taxol, cisplatin of different concentration gradients were directly added to the semi-suspending cells (K562 and K562/Adr). The adherent cells were cultured for 24 hours after inoculation so that they could adhere completely, and then the drugs mentioned above in different concentrations were added. There were six parallel repeated wells for every concentration gradient. The medium was added up to a final volume of 200 μl per well. The cells were cultured at the condition of 37° C., saturated humidity, 5% $CO_2$ for 68 hours. 50 μl MTT (2 mg/mL) per well was added. The 96-well plate was centrifuged and the supernatant was removed. Then 120 μl DMSO per well was added and vibrated by vibrator. The OD value was determined at a wavelength of 590 nm by enzyme labeling instrument after the crystal was dissolved completely.

The calculating method: $IC_{50}$=drug concentration when the inhibitory rate was 50%.

Drug resistant factor (RF)=the $IC_{50}$ of the drug resistant cells/the $IC_{50}$ of the sensitive cells.

The results of the drug resistance determination of drug resistant cell lines to conventional chemotherapeutic drugs are shown in Table 2 ($IC_{50}$: μg/mL).

TABLE 2

|  | K562 | K562/Adr | RF | KB | KBv200 | RF | MCF-7 | MCF-7/Adr | RF |
|---|---|---|---|---|---|---|---|---|---|
| Adr | 0.215 ± 0.152 | 14.06 ± 0.350 | 65.39 | 0.490 ± 0.176 | 16.28 ± 1.03 | 33.22 | 0.312 ± 0.143 | 18.96 ± 0.67 | 59.07 |
| VCR | 0.218 ± 0.011 | 12.15 ± 0.576 | 55.73 | 0.153 ± 0.092 | 21.34 ± 1.21 | 139.5 | 0.096 ± 0.014 | 18.6 ± 1.75 | 193.75 |
| Taxol | 0.0247 ± 0.001 | 0.932 ± 0.092 | 37.72 | 0.032 ± 0.001 | 1.348 ± 0.002 | 42.12 | 0.0415 ± 0.003 | 0.743 ± 0.21 | 17.65 |
| DDP | 0.2274 ± 0.078 | 1.075 ± 0.5646 | 4.727 | 0.5509 ± 0.094 | 7.785 ± 0.6536 | 14.13 | 0.6453 ± 0.1675 | 7.342 ± 0.764 | 11.38 |

2. Determination of Glyoxalase I (GLO1) Activity

The cells were repeatedly frozen-thawed in PBS containing 1 mM PMSF, broken up by ultrasonication, centrifuged at 12000 for 20 minutes and then the supernatant was collected. A mixture of 7.9 mM MG, 1 mM glutathione, 14.6 mM $MgSO_4$, 182 mM imidazole-HCl (PH7.0) was used to determine the GLO1. The OD value was determined at 240 nm. The results are shown in Table 1.

TABLE 1

| | Cell line | | | | | |
|---|---|---|---|---|---|---|
| | K562 | K562/Adr | KB | KBv200 | MCF-7 | MCF-7/Adr |
| OD value | 0.22 | 1.21 | 0.31 | 1.47 | 0.16 | 1.46 |

The results indicate that one of the drug-resistant mechanisms of the cell lines tested is related to the increased activity of GLO1.

The results showed that all the drug resistant cell lines tested have cross drug resistances among the conventional chemotherapeutic drugs, that is, multi-drug resistance.

EXAMPLE 3

Cytologic Effect Evaluation of PA Derivatives—the Ability of Inhibiting the Growth of Drug Resistant Cell Lines Methods: $1 \times 10^3$ cells per well were inoculated onto a 96-well plate. PA was added to K562/Adr directly and to KBV200 and MCF-7/Adr after adhesion. The concentrations of the drugs were 0, 0.1, 0.5, 1, 5, 10, 20, 40, 80, 160 μg/mL. MTT was determined according to the method of example 2 and the $IC_{50}$ was calculated. The experiment was repeated three times.

The results of the determination of growth inhibiting effect of PA on drug resistant cells are shown in Table 3 ($IC_{50}$ (μg/mL)).

TABLE 3

|  | S1 | S2 | S3 | S4 | S5 | S6 | S7 | S8 |
|---|---|---|---|---|---|---|---|---|
| K562/Adr | 21.35 ± 1.092 | 41.44 ± 3.528 | 39.16 ± 1.577 | 32.38 ± 1.13 | 18.31 ± 0.762 | 29.78 ± 0.995 | 20.44 ± 2.607 | 31.27 ± 1.871 |
| KBv200 | 38.67 ± 2.133 | 26.36 ± 1.980 | 27.44 ± 1.065 | 32.45 ± 1.032 | 29.83 ± 1.048 | 35.24 ± 2.151 | 36.90 ± 2.192 | 38.56 ± 2.17 |
| MCF-7/Adr | 37.43 ± 3.147 | 29.45 ± 2.801 | 33.99 ± 3.763 | 47.32 ± 2.118 | 39.34 ± 2.143 | 44.50 ± 3.989 | 39.59 ± 4.606 | 43.21 ± 3.136 |

The results showed that PA derivatives have no significant cytotoxic effects at the concentration about 10 μg/mL.

EXAMPLE 4

Cytologic Effect Evaluation of PA Derivatives—Sensitizing Effect to Conventional Chemotherapeutic Drugs The cells at logarithmic phase were collected and added into RPMI 1640 medium (containing 10% fetal bovine serum) to make cell suspensions. The cell suspension was added to 96-well plate at 100 μl per well, and the cell number was $2 \times 10^3$ (suspending cells) or $1 \times 10^3$ (adherent cells) per well. After inoculation, the suspending cells were adapted for half an hour on the plate and the adherent cells were cultivated to allow adhesion before the drugs were added. The control groups (Ctrl) were added with anti-tumor drugs but without PA. The drug concentration of each PA group was 10 μg/mL. The concentrations of chemotherapeutic drugs increased from 0.001 μg/mL to 20 μg/mL. There Were six parallel repeated wells for every concentration gradient. RPMI 1640 was added up to a finally volume of 200 μl per well. The cells were cultured at the condition of 37° C., saturated humidity, 5% $CO_2$ for 68 hours. The MTT was determined and the $IC_{50}$ was calculated as in example 4.

The formula of resistant factor: Resistant Factor (RF)=the $IC_{50}$ without sensitizer/the $IC_{50}$ with sensitizer.

The results of the determination of sensitizing effect of PA (10 μg/mL) on K562/Adr cells are shown in table 4.

The results of the determination of sensitizing effect of PA (10 μg/mL) on KBv200 cells are shown in table 5.

The results of the determination of sensitizing effect of PA (10 μg/mL) on MCF-7/Adr cells are shown in table 6.

TABLE 4

|  | Ctrl | S1 | RF (Ctrl/S1) | S2 | RF (Ctrl/S2) |
|---|---|---|---|---|---|
| Vin | 12.13 ± 0.3492 | 1.599 ± 0.2788 | 6.214 | 5.690 ± 0.0754 | 1.757 |
| Adr | 7.674 ± 0.1603 | 0.1051 ± 0.0049 | 34.99 | 0.0748 ± 0.0109 | 41.12 |
| Taxol | 0.8225 ± 0.0073 | 0.0342 ± 0.0073 | 24.04 | 0.0778 ± 0.0062 | 10.57 |
| DDP | 5.311 ± 0.4429 | 1.023 ± 0.3232 | 5.116 | 0.9321 ± 0.2372 | 5.698 |

|  | S3 | RF (Ctrl/S3) | S4 | RF (Ctrl/S4) | S5 | RF (Ctrl/S5) |
|---|---|---|---|---|---|---|
| Vin | 2.476 ± 0.6062 | 4.899 | 1.886 ± 0.1602 | 6.432 | 3.901 ± 0.6772 | 3.109 |
| Adr | 0.5507 ± 0.049 | 13.93 | 1.214 ± 0.0707 | 6.349 | 1.225 ± 0.515 | 6.264 |
| Taxol | 0.1433 ± 0.022 | 5.740 | 0.3410 ± 0.0105 | 2.412 | 0.3883 ± 0.0436 | 2.117 |
| DDP | 2.371 ± 0.8736 | 2.239 | 1.766 ± 0.3346 | 3.007 | 2.5239 ± 0.1452 | 2.104 |

|  | S6 | RF (Ctrl/S6) | S7 | RF (Ctrl/S7) | S8 | RF (Ctrl/S8) |
|---|---|---|---|---|---|---|
| Vin | 6.620 ± 0.3211 | 1.833 | 3.061 ± 0.6332 | 3.963 | 1.532 ± 0.3442 | 7.918 |
| Adr | 1.228 ± 0.699 | 6.249 | 0.9294 ± 0.1834 | 8.257 | 4.273 ± 0.8435 | 1.796 |
| Taxol | 0.5126 ± 0.1053 | 1.641 | 0.5306 ± 0.1165 | 1.550 | 0.2346 ± 0.0559 | 3.506 |
| DDP | 3.875 ± 0.7835 | 1.371 | 3.213 ± 0.5643 | 0.653 | 1.9504 ± 0.3423 | 2.722 |

TABLE 5

|  | Ctrl | S1 | RF (Ctrl/S1) | S2 | RF (Ctrl/S2) |
|---|---|---|---|---|---|
| Vin | 10.74 ± 0.9923 | 0.8245 ± 0.2934 | 13.03 | 0.9422 ± 0.2002 | 11.40 |
| Adr | 4.391 ± 0.3356 | 0.4277 ± 0.156 | 10.27 | 0.3591 ± 0.0429 | 12.23 |
| Taxol | 1.015 ± 0.0421 | 0.1935 ± 0.0045 | 5.245 | 0.0939 ± 0.0054 | 10.83 |
| DDP | 5.868 ± 0.2438 | 0.7278 ± 0.0569 | 8.063 | 2.121 ± 0.3337 | 2.767 |

|  | S3 | RF (Ctrl/S3) | S4 | RF (Ctrl/S4) | S5 | RF (Ctrl/S5) |
|---|---|---|---|---|---|---|
| Vin | 1.741 ± 0.3922 | 6.169 | 0.826 ± 0.0412 | 13.02 | 5.142 ± 0.0400 | 2.088 |
| Adr | 0.2315 ± 0.9545 | 18.97 | 0.8237 ± 0.2253 | 5.331 | 0.2591 ± 0.0426 | 16.95 |
| Taxol | 0.3983 ± 0.08876 | 2.548 | 0.1582 ± 0.0211 | 6.416 | 0.3164 ± 0.0103 | 13.88 |
| DDP | 0.8164 ± 0.0103 | 7.188 | 0.8406 ± 0.0501 | 6.981 | 0.1010 ± 0.0137 | 3.208 |

|  | S6 | RF (Ctrl/S6) | S7 | RF (Ctrl/S7) | S8 | RF (Ctrl/S8) |
|---|---|---|---|---|---|---|
| Vin | 3.214 ± 0.1903 | 3.342 | 1.456 ± 0.3952 | 7.376 | 1.4662 ± 0.1152 | 7.326 |
| Adr | 1.912 ± 0.2206 | 2.297 | 1.826 ± 0.5297 | 2.405 | 1.212 ± 0.4603 | 3.623 |
| Taxol | 0.1164 ± 0.0103 | 8.72 | 0.196 ± 0.0136 | 5.179 | 0.2623 ± 0.0757 | 3.87 |
| DDP | 2.238 ± 0.3891 | 2.622 | 0.988 ± 0.2551 | 5.939 | 1.3412 ± 0.0885 | 4.375 |

TABLE 6

| | Ctrl | S1 | RF (Ctrl/S1) | S2 | RF (Ctrl/S2) |
|---|---|---|---|---|---|
| Vin | 14.07 ± 1.953 | 1.266 ± 0.4328 | 11.12 | 2.255 ± 0.9912 | 6.239 |
| Adr | 6.321 ± 0.7753 | 0.5572 ± 0.3056 | 11.34 | 0.911 ± 0.2902 | 6.939 |
| Taxol | 0.906 ± 0.213 | 0.3374 ± 0.045 | 2.685 | 0.0889 ± 0.024 | 10.19 |
| DDP | 7.708 ± 1.077 | 2.283 ± 0.6489 | 3.376 | 3.005 ± 0.1776 | 2.565 |
| | S3 | RF (Ctrl/S3) | S4 | RF (Ctrl/S4) | S5 | RF (Ctrl/S5) |
| Vin | 3.531 ± 0.5230 | 4.008 | 0.541 ± 0.4781 | 26.01 | 2.029 ± 0.6483 | 6.934 |
| Adr | 1.522 ± 0.3126 | 4.153 | 2.030 ± 0.7546 | 3.114 | 1.2591 ± 0.6673 | 5.02 |
| Taxol | 0.2803 ± 0.0432 | 3.232 | 0.2117 ± 0.0211 | 4.279 | 0.058 ± 0.053 | 15.62 |
| DDP | 1.149 ± 0.4103 | 6.708 | 1.504 ± 0.5031 | 5.125 | 1.710 ± 0.9137 | 4.508 |
| | S6 | RF (Ctrl/S6) | S7 | RF (Ctrl/S7) | S8 | RF (Ctrl/S8) |
| Vin | 1.064 ± 0.1903 | 13.22 | 3.673 ± 0.5122 | 3.831 | 1.466 ± 0.1152 | 9.597 |
| Adr | 0.5022 ± 0.2160 | 12.59 | 0.4476 ± 0.1297 | 14.12 | 1.212 ± 0.4603 | 5.639 |
| Taxol | 0.2304 ± 0.0307 | 3.932 | 0.129 ± 0.0146 | 7.023 | 0.562 ± 0.0737 | 1.612 |
| DDP | 3.035 ± 0.621 | 2.539 | 1.183 ± 0.3503 | 6.516 | 1.203 ± 0.3302 | 6.407 |

EXAMPLE 5

Cytologic Effect Evaluation of PA Derivatives—Sensitizing Effect for Cell Death Induced by Chemotherapeutic Drugs Cell inoculation and drug induction were performed as in example 2. Forty-eight hours later, 5 μL of trypan blue (4 mg/mL) was added to each well. Five minutes later, the cells were observed under microscope. Five hundred of cells were counted per well. The cells stained with blue were dead cells. The survival rate of cells was calculated.

Cell survival rate(%)=[1−dead cells(blue)/500]*100.

Figure 3:
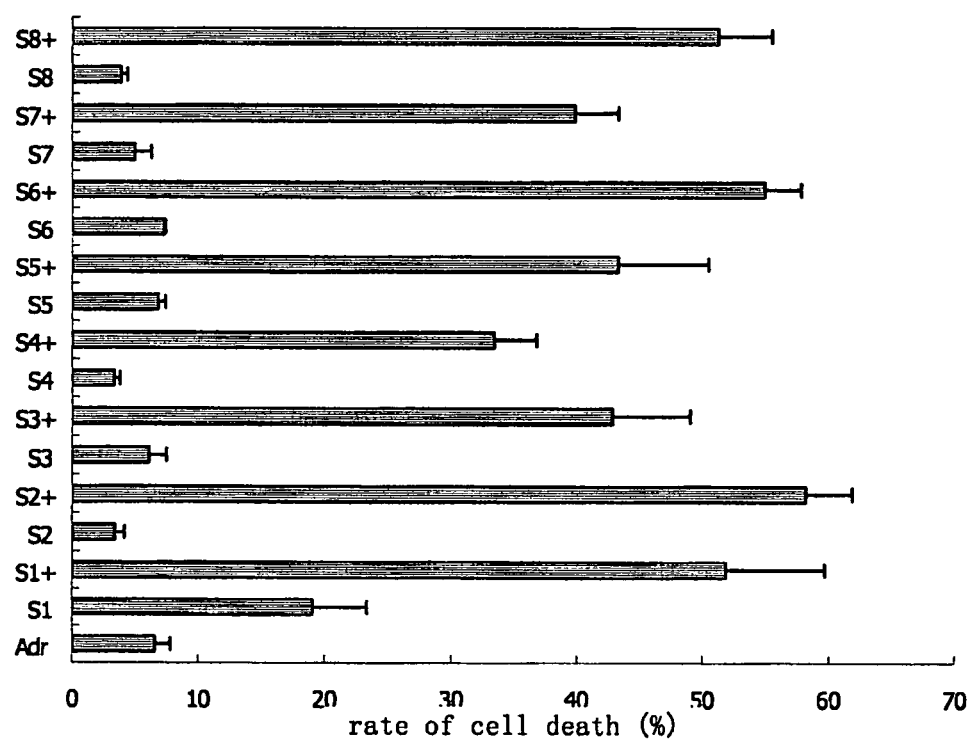
FIG. 3 shows the enhancing effects of PA derivatives on Adr-induced cell death in MCF-7/Adr cells.

The sensitizing effect of PA derivatives for cell death induced by Adriamycin was shown in FIG. 3. The concentration of each compound of S1-S8 was 10 μg/mL. The concentration of Adr was 2.5 μg/mL. S1+-S8+ represents the combined use of S (10 μg/mL) and Adr (2.5 μg/mL). The results showed that PA derivatives could notably enhance the cell death induced by Adr.

EXAMPLE 6

FACS Determination of Sensitizing Effect of the PA Derivatives for Apoptosis Induced by Chemotherapeutic Drugs MCF-7/Adr was inoculated onto a 6-well plate (1×10⁶ cells/well). The cells were cultured for 24 hours, and then PA and chemotherapeutic drugs were added as described above. Cells were cultured for another 72 hours. The cells were digested by 0.25% trysin and collected. The cell pellet was fixed by 70% of precooled ethanol and preserved at 4° C. The samples were washed by PBS for 3 times, digested by RNase (1 g/mL) for 15 minutes, stained by propidium iodide (PI, 50 mg/L) for 30 minutes, and then measured by Fluorescence Activated Cell Sorter and the percent of death cells was calculated.

Figure 4:
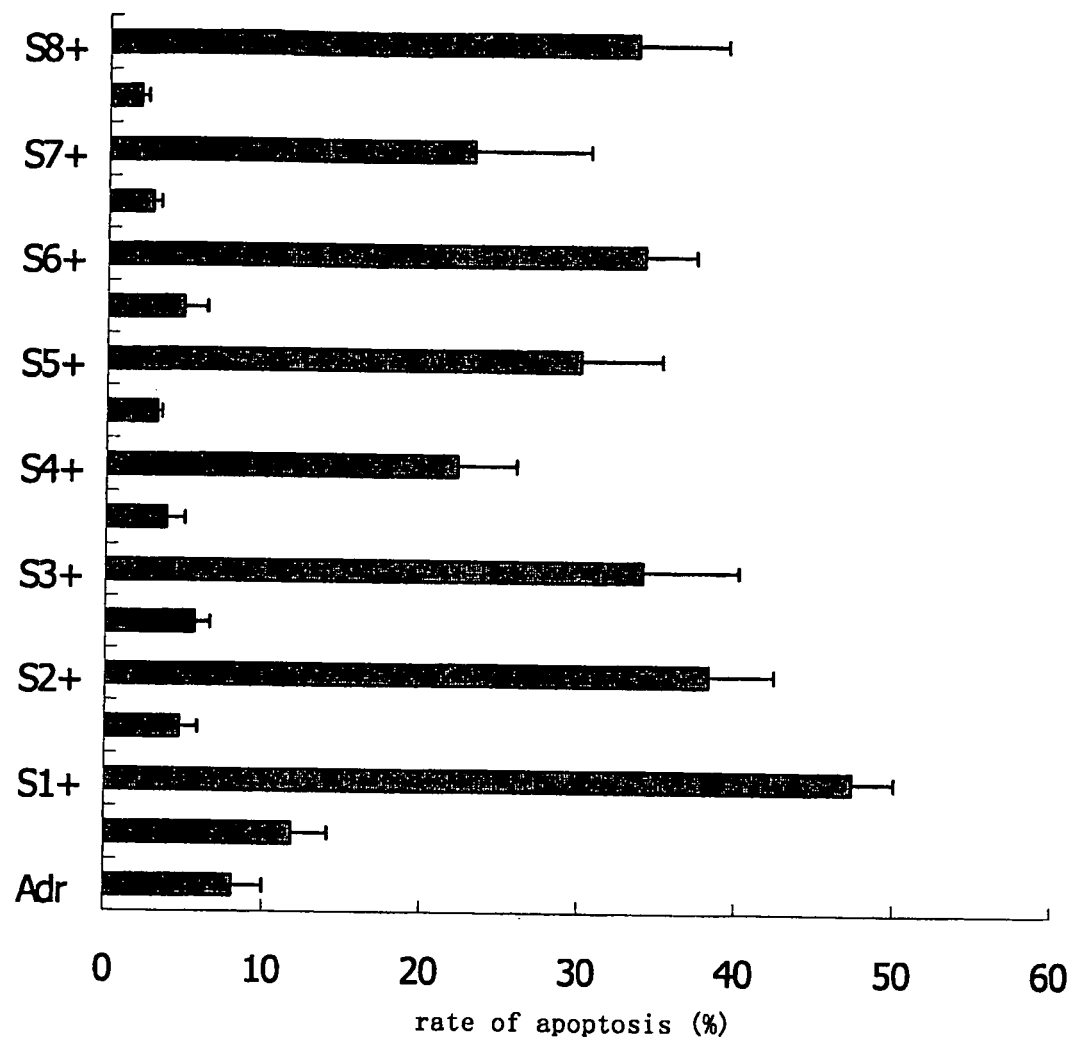
FIG. 4 shows the potentiated effects of PA derivatives in combination with Adr on Adr-induced apoptosis in MCF-7/Adr cells measured by FACS.

The results are shown in FIG. 4. The concentration of Adr was 2.5 μg/mL. The concentration of PA was 10 μg/m. S1+-S8+ represents the combined use of S (10 μg/mL) and Adr (2.5 μg/mL). The results showed that PA derivatives could notably sensitize the cell death induced by Adr.

All the documents cited herein are incorporated into the invention by reference, as if each of them is individually incorporated. Further, it would be appreciated that, in the above teachings of the invention, the skilled in the art could make various changes or modifications to the invention, and these equivalents would still be within the scope of the invention defined by the appended claims of the application.

The invention claimed is:

1. A method of treating a tumor having resistance to an anti-cancer drug in a subject, wherein the tumor exhibits either (1) overexpression of at least one selected from the group consisting of P-gp and Bcl-2, or (2) over-activity of glyoxalase I, the method comprising: administering to the subject, the anti-cancer drug and a therapeutically effective amount of at least one phthalide compound selected from the group consisting of

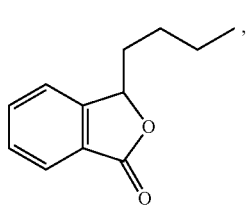

(1)

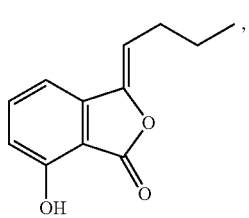

(2)

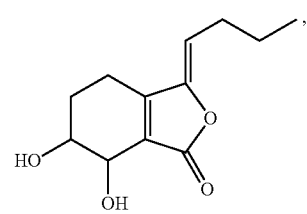

(3)

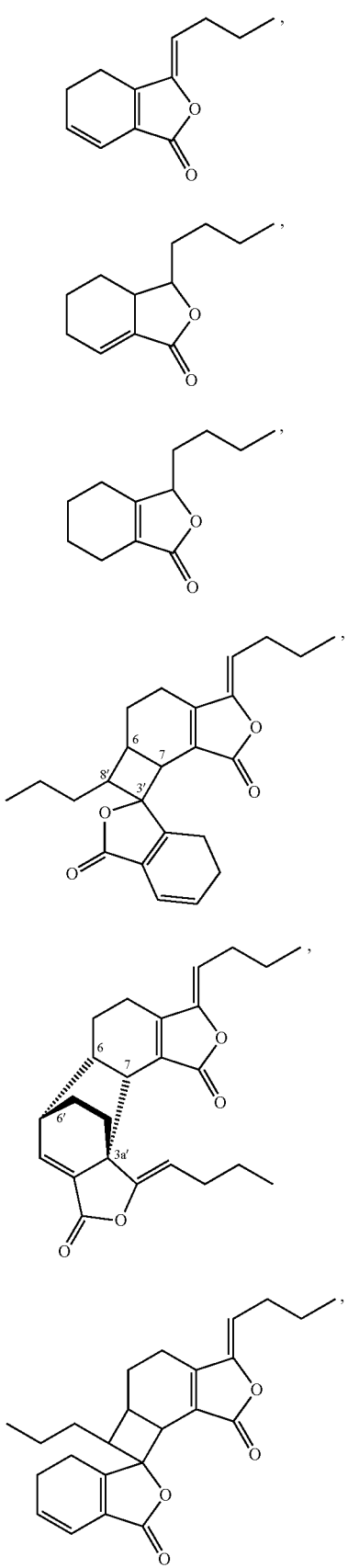
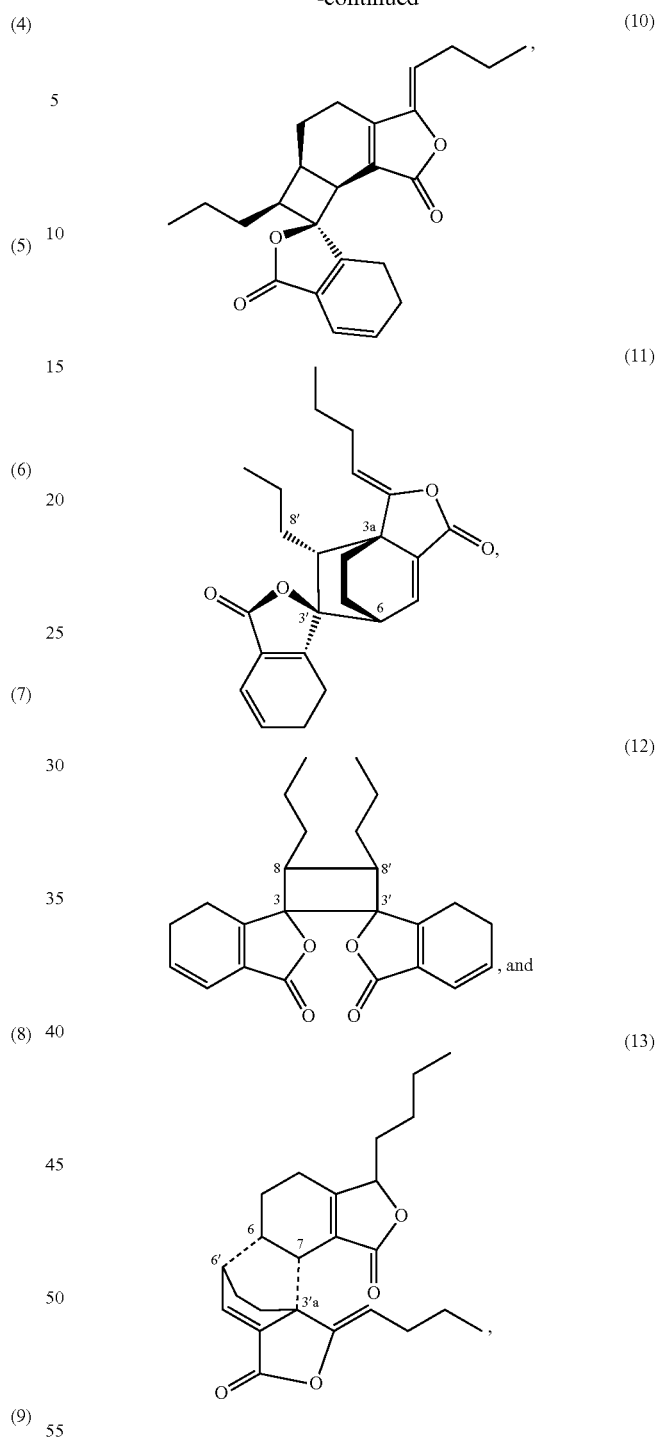

wherein the amount is an amount effective for inhibiting either (1) overexpression of at least one selected from the group consisting of P-gp and Bcl-2, or (2) overactivity of glyoxalase I in the subject.

2. The method of claim 1, further comprising administering at least one anti-tumor drug selected from the group consisting of: doxorubicin; Vincristine; paclitaxel; Cisplatin; Actinomycin; Bleomycin; Busulfan; Capecitabine; Carboplatin; Carmustine; Chlorambucil; Cyclophosphamide; Cytarabine; Daunorubicin; Epirubicin; Etop1; Vepeside; Etoposide; Fludarabine; Fluorouracil; Gemcitabine; Trastuzumab; Hydroxycarbamide; Idarubicin; Ifosfamide; Irinotecan;

Lomustine; Melphalan; Mercaptopurine; Methotrexate; Mitomycin; Mitoxantrone; Dihydroxyanthraquinone; Oxaliplatin; Procarbazine; Methylhydrazine; rituximab; Steroid; Streptozocin; Docetaxel; Thioguanine; Thiotepa; Ledertepa; Tespamin; Raltitrexed; Topotecan; Treosulfan; Uracil; Vinblastine; Vinca alkaloid; Vindesine; Vinorelbine; Hydroxycamptothecin; and mixtures thereof.

3. The method of claim 2, wherein said at least one anti-tumor drug is used to treat tumors selected from the group consisting of: non-small cell lung cancer, prostate cancer, intestinal cancer, hepatocarcinoma, leukaemia, myeloma, lymphoma, mammary cancer, ovary cancer, gastric cancer, esophagus cancer, colonic cancer, or sarcoma.

4. The method of claim 1, wherein the anti-cancer drug is selected from the group consisting of: doxorubicin; Vincristine; paclitaxel; Cisplatin; Actinomycin; Bleomycin; Busulfan; Capecitabine; Carboplatin; Carmustine; Chlorambucil; Cyclophosphamide; Cytarabine; Daunorubicin; Epirubicin; Etop1; Vepeside; Etoposide; Fludarabine; Fluorouracil; Gemcitabine; Trastuzumab; Hydroxycarbamide; Idarubicin; Ifosfamide; Irinotecan; Lomustine; Melphalan; Mercaptopurine; Methotrexate; Mitomycin; Mitoxantrone; Dihydroxyanthraquinone; Oxaliplatin; Procarbazine; Methylhydrazine; rituximab; Steroid; Streptozocin; Docetaxel; Thioguanine; Thiotepa; Ledertepa; Tespamin; Raltitrexed; Topotecan; Treosulfan; Uracil; Vinblastine; Vinca alkaloid; Vindesine; Vinorelbine; and Hydroxycamptothecin.

5. The method of claim 1, wherein the at least one phthalide compound is

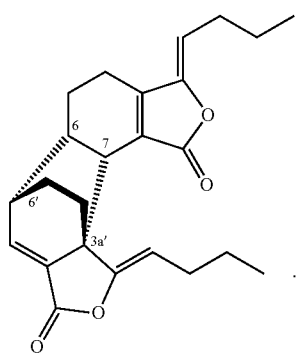

(8)

* * * * *